(12) United States Patent
Waizenegger

(10) Patent No.: US 9,480,513 B2
(45) Date of Patent: Nov. 1, 2016

(54) CLAMPING ELEMENT FOR SETTING A BONE FRACTURE AS WELL AS MODULAR FIXATION DEVICE COMPRISING SAME AND METHOD FOR PRODUCING SAME

(75) Inventor: Markus Waizenegger, Mühlheim a.d. Donau (DE)

(73) Assignee: HIPP MEDICAL AG, Kolbingen (DE)

( * ) Notice: Subject to any disclaimer, the term of this patent is extended or adjusted under 35 U.S.C. 154(b) by 577 days.

(21) Appl. No.: 14/002,240

(22) PCT Filed: Jan. 25, 2012

(86) PCT No.: PCT/EP2012/000329
§ 371 (c)(1),
(2), (4) Date: Oct. 25, 2013

(87) PCT Pub. No.: WO2012/116772
PCT Pub. Date: Sep. 7, 2012

(65) Prior Publication Data
US 2014/0046378 A1    Feb. 13, 2014

(30) Foreign Application Priority Data
Mar. 2, 2011   (DE) ........................ 10 2011 001 016

(51) Int. Cl.
*A61B 17/04*      (2006.01)
*A61B 17/86*      (2006.01)
(Continued)

(52) U.S. Cl.
CPC .............. *A61B 17/82* (2013.01); *A61B 17/68* (2013.01); *A61B 17/8004* (2013.01); *A61B 17/8085* (2013.01); *A61B 2017/681* (2013.01); *Y10T 29/49995* (2015.01); *Y10T 83/0524* (2015.04)

(58) Field of Classification Search
CPC .. A61B 17/68; A61B 17/681; A61B 17/685; A61B 17/8004; A61B 17/8014; A61B 17/8052; A61B 17/8057; A61B 17/8085
USPC ......................................................... 606/302
See application file for complete search history.

(56) References Cited

U.S. PATENT DOCUMENTS 2,580,821 A    1/1952  Toufick
7,335,200 B2   2/2008  Carli
(Continued)

FOREIGN PATENT DOCUMENTS

DE        20001879 U1   3/2000
WO     2004034916 A1    4/2004
(Continued)

*Primary Examiner* — Kevin T Truong
*Assistant Examiner* — Si Ming Ku
(74) *Attorney, Agent, or Firm* — Abel Law Group, LLP

(57) ABSTRACT

Disclosed is a clamping element for setting a bone fracture. The element comprises a closed contoured body which has a substantially hollow cross-section and is enclosed by a peripheral wall. The contoured body has two opposite receiving portions at the end faces thereof, the receiving portions being intended to receive fixing elements which can be pushed through the body, and has two lateral flanks having angled portions. The peripheral wall of the contoured body is resiliently deformable at least in sections, in particular in the region of the receiving portions on the end faces of same and in the region of the lateral angled portions. A defined resilient behavior of the clamping element can be impressed via the angled portions in such a way that a predetermined tension can be generated between the receiving portions. Also disclosed are a method for producing the clamping element and a setting device for using said clamping element.

17 Claims, 11 Drawing Sheets

(51) Int. Cl.
*A61F 2/08* (2006.01)
*A61B 17/82* (2006.01)
*A61B 17/68* (2006.01)
*A61B 17/80* (2006.01)

(56) References Cited

U.S. PATENT DOCUMENTS

| | | |
|---|---|---|
| 7,763,056 B2 | 7/2010 | Dalton |
| 7,799,055 B2 | 9/2010 | Lim |
| 8,221,478 B2 | 7/2012 | Patterson et al. |
| 2004/0073215 A1 | 4/2004 | Carli |
| 2005/0043732 A1 | 2/2005 | Dalton |
| 2005/0209593 A1 | 9/2005 | Kolb |
| 2006/0058796 A1 | 3/2006 | Hartdegen et al. |
| 2006/0081553 A1 | 4/2006 | Patterson et al. |
| 2007/0270820 A1 | 11/2007 | Dickinson et al. |
| 2008/0021458 A1 | 1/2008 | Lim |
| 2009/0036930 A1 | 2/2009 | Allison |
| 2009/0163954 A1 | 6/2009 | Kwak |
| 2010/0036430 A1 | 2/2010 | Hartdegen et al. |
| 2010/0145386 A1 | 6/2010 | Greenhalgh et al. |

FOREIGN PATENT DOCUMENTS

| | | |
|---|---|---|
| WO | 2005086708 A2 | 9/2005 |
| WO | 2006031692 A1 | 3/2006 |
| WO | 2007127628 A2 | 11/2007 |
| WO | 2008005740 A1 | 1/2008 |
| WO | 2009039430 A1 | 3/2009 |

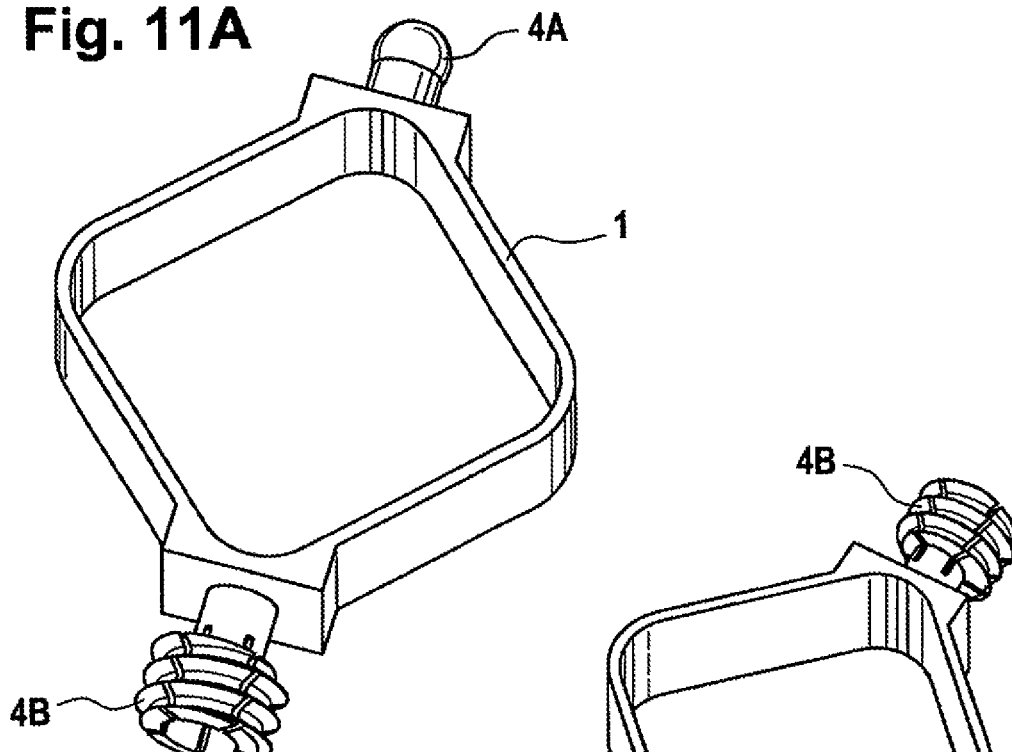
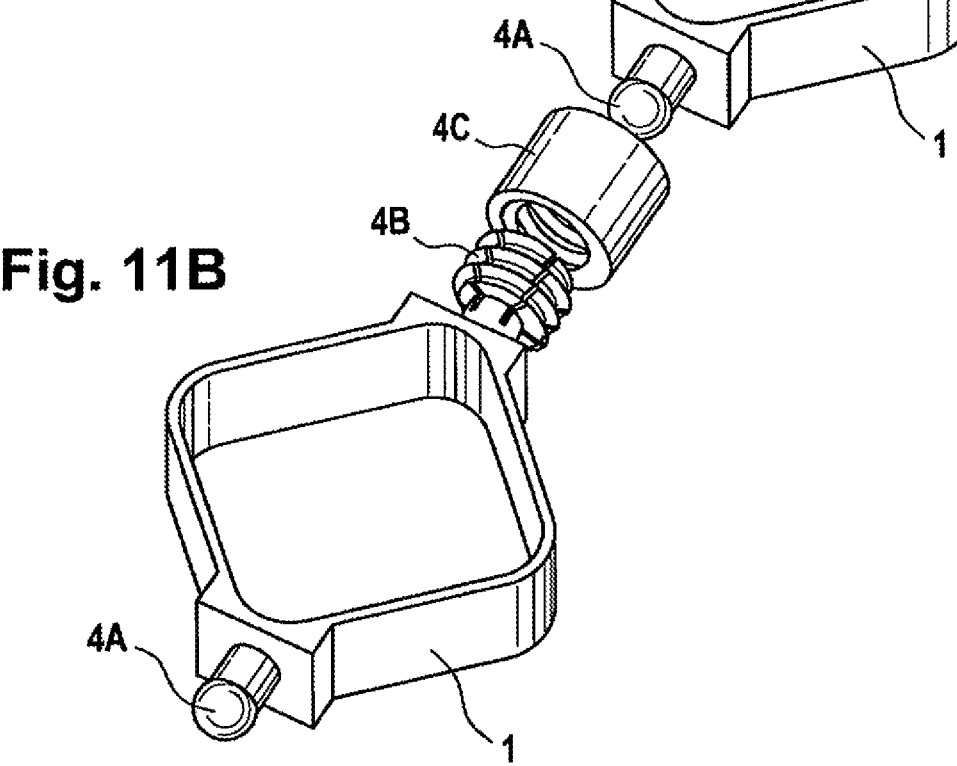

CLAMPING ELEMENT FOR SETTING A BONE FRACTURE AS WELL AS MODULAR FIXATION DEVICE COMPRISING SAME AND METHOD FOR PRODUCING SAME

BACKGROUND OF THE INVENTION

1. Field of the Invention

The invention relates to a clamping element for setting or fixation of a bone fracture as well as to a setting device comprising such a clamping element. The invention also relates to a method for producing such a clamping element.

2. Discussion of Background Information

When a bone fracture is immobilized insufficiently, a callus formation, i.e. a tyloma-like thickening of the ends of the fracture from overgrowing bone tissue, can occur. In order to avoid such an indirect fracture healing via a callus, bone plates are used which are applied and attached to the outer surface of a broken bone so that the fracture site is set, i.e. fixed, during the healing process.

For such applications for the treatment of bone fractures, from prior art there are mainly known rigid, metallic bone plates formed in a planar manner and having bores which are screwed at the opposite sides of a fracture. For the fastening of such settings or fixations, usually so-called cortical screws are used which are screwed into the outer bone tissue, the so-called cortical layer, which has the highest strength of the bone. The setting or fixation ensures that the ends of the fracture cannot move with respect to each other and that newly formed bone tissue can accumulate such that it will not be subjected to any loads.

Furthermore, it is assumed that the healing process of a fracture can be influenced beneficially when a compression is applied onto the joined fracture site. Thereby a particularly close adaption, i.e. a very small clearance over which the ends of the fracture grow towards each other again, is effected.

With respect thereto, U.S. Pat. No. 7,763,056 B2 discloses a two-part bone plate, the two halves of which can move towards each other by means of an axial guide. For the production of a compression, various arrangements of tension springs are proposed which are fixed at the two halves. The bone plate is constructed of several components and, consequently, is cost-intensive to produce.

Furthermore, there are also known vertebral bone plates which are not completely rigid but enable a mutual approaching of vertebral bodies and a swinging or twisting of the vertebral bodies with respect to each other to a limited extent. Thereby for example the regeneration of a damaged intervertebral disk or the healing of a fracture of a vertebral body can be assisted. With respect thereto, the utility model specification DE 200 01 879 U1 and the published patent application WO 2004/034916 A1 disclose bone plates with sections which are shaped in a meandering manner and which furnish the structure of the bone plate with a multi-directional flexibility.

Furthermore, the published patent application WO 2005/086708 A2 describes various embodiments of bone plates for the anterior cervical spine, which enable an axial and a lateral flexibility and which have a structure with intermediate sections which, when subjected to a load in the axial direction, bend laterally.

Such vertebral bone plates which are known from prior art shall, however, prevent any compression between two vertebral bodies in order to relieve the intervertebral disk and to prevent any impairment or damage of the spinal nerves. Consequently, they are not suitable for a compression-producing setting of a bone fracture, and, moreover, due to the manifold requirements of said particularly delicate application, they have a complex structure. Also the bone plates cited at the beginning are of a relatively complex design and, correspondingly, are cost-intensive to produce.

Accordingly, in medical care only a limited circle of patients or of types of fractures has benefited from the advantageous application of a compression-producing setting until now.

Thus, the invention is based on the object to provide a clamping element for a setting or fixation device that can be produced at particularly low costs in order to expand the field of application of compression-producing settings or fixations, and on the object to develop a corresponding method by means of which the clamping element can be produced at low costs. Moreover, the invention is also based on the object to provide a setting or fixation device in which the clamping element can be used.

SUMMARY OF THE INVENTION

The object is solved by the clamping element as well as by the setting or fixation device and the method set forth in the appended claims.

The clamping element is characterized by a closed contoured body which has a substantially hollow cross-section and is enclosed by a peripheral wall, which is in particular of a substantially constant thickness. The contoured body has two opposite receiving portions at the end faces of said contoured body, said receiving portions being intended to receive fixing means, preferably cortical screws, which can be pushed through the contoured body, and has two lateral flanks having angled portions, wherein the peripheral wall of the contoured body is resiliently deformable at least in sections, in particular in the region of the receiving portions on the end faces of same and in the region of the lateral angled portions. A defined resilient behavior of the clamping element can be impressed via the angled portions in such a way that a predetermined tension can be generated between the receiving portions.

The desired resiliency of the clamping element in its longitudinal direction is directly proportional to a transverse contraction of the clamping element. In a clamping element with e.g. a rhomboidal geometry, the ratio between longitudinal expansion and transverse contraction can be influenced in a simple manner via the angle of curvature of the angled portions and of the receiving portions at the end faces. Due to the simple design of the clamping element, the setting device can be manufactured in a particularly cost-effective manner. Thereby, the potential field of application of compression-producing settings for the acceleration of the healing process is extended with respect to the potential circle of patients on the one hand and also to relatively uncritical bone fractures on the other hand.

The setting or fixation device is characterized by the fact that it comprises at least one clamping element and at least two fixing means, preferably cortical screws, which can be placed into the bone in the region of the ends of the fracture.

When the setting or fixation device is used, it is intended to produce a compression at a fracture site by means of a clamping element according to the invention. To this end, prior to the insertion of the clamping element a pressure is applied onto the lateral flanks or the angled portions in order to initiate a transverse contraction of the clamping element. The effected transverse contraction is associated with a longitudinal expansion of the clamping element. When, now, the fixing means are enclosed by the clamping element, the pretension or prestress of the longitudinal expansion effects a tractive force between the fixing means. Accordingly, no additional constructive means, as for instance a tension spring or a screw connection calibrated to a tensile stress, are required for the production of a compression.

Advantageous further developments are described in the dependent claims.

According to one embodiment, the closed contoured body of the clamping element can substantially be of an oval, rhomboidal, double-rhomboidal or spectacles-shaped design. In case of the rhomboidal shape or the oval shape, the angled portions of the lateral flanks point outwards. Said design allows for a large possible range of angles of curvature.

In another embodiment, the angled portions point inwards so that the width of the clamping element is reduced towards the middle section of the clamping element. Hence, a spectacles-shaped form of the clamping element is obtained the width of which depends on the radius of curvature of the receiving portions or on the width of a fixing means to be received or of a clamping sleeve. By the slim design, the required space in the body tissue is reduced, and narrower alignment angles between adjacent clamping elements at connection points are rendered possible.

In a further embodiment, the lateral flanks can comprise three opposed angled portions, respectively, wherein the mean angled portion points inwards, respectively. For a rhomboidal or spectacles-shaped embodiment, the structure of the clamping element is substantially preset, in particular when a functionally optimized range of the angle of curvature of the angled portions is observed. The arrangement of several alternating angled portions enables a greater freedom of design with respect to the linear dimension and the width dimension of the clamping element.

In another embodiment, the closed contoured body of the clamping element can have a curvature with regard to the plane of extension of the contour. In this connection, the curvature can in particular correspond to the surface of the respective bone. Said anatomic adaptation is for instance intended for fields of application like the knee cap (patella) or a radial fastening on a tubular bone for the treatment of a torsion fracture with a fracture line extending obliquely or in a slightly helical manner.

For the treatment of comminuted fractures or of bones with a particular anatomy, normally the use of several individual bone plates or individually shaped bone plates is required. A setting or fixation with several individual bone plates involves the use of a higher number of screws which have to be inserted at the limited area of bone fragments in the region of the fracture margins. Thereby the complexity, the expenditure in time, and the risk of the surgical operation are increased. An individual manufacture of bone plates is cost-intensive and, in particular, entails waiting periods.

In the present clamping element according to the invention, the wall can comprise openings and/or cutaway portions in the region of the receiving portions. Said openings and/or cutaway portions are formed such that by a groove structure and/or a tongue structure of wall sections a complementary fit is provided by means of which the contours of the adjacent clamping elements can be brought into an overlapping position with respect each other.

The openings and cutaway portions allow for the linking of several clamping elements in the sense of a tongue and groove connection. Thus, by the combination of several clamping elements, for instance also of such clamping elements with different dimensions, curvatures and designs, a modular configuration in the manner of a modular construction system is provided, by means of which a setting device according to the invention can be individually adapted in a simple manner to the structure of a fracture, in particular of a comminuted fracture, as well as to the local anatomic conditions.

As compared with a plurality of individual bone plates, by the combination of several clamping elements the number of the required fastening points can be reduced. This is particularly advantageous for small bone fragments, and, moreover, also reduces the surgical expenditure enormously. In comparison with individually manufactured bone plates, by the modular configuration possibility a rapid treatment of complicated fractures can be achieved.

In a further embodiment, coupling elements or a ball element or a spherical clamping part can be provided at the outer surface of the wall, by means of which adjacent clamping elements can be connected with each other preferably in such a manner that they can be rotated with respect to each other in a ball-joint manner and/or that they are fixed in their positions relative to each other. Said embodiments represent possibilities for the combination of several clamping elements, which do not require an overlapping of said clamping elements and which can be fixed in a certain position of the clamping elements with respect to each other. Therefore, for instance a chaining of clamping elements via the lateral flanks can be realized. In this connection, the embodiment of a ball joint which enables a clamping connection offers a large degree of flexibility for a multidirectional combination.

In another embodiment, fastening eyes can be provided at the wall, through which the fixing means can be pushed. Said design offers another possibility for an easy fastening of a clamping element.

In a further embodiment, two limiting bars pointing towards each other can be formed at two opposite wall sections, wherein the ends of said limiting bars get into contact with each other when the clamping element is deformed. The limiting of a deformation path initiated due to external forces provides a protection against deformations which would go beyond the resilient range of the clamping element and would lead to permanent changes of the original dimensions of the clamping element. Furthermore, the limiting stop can also be used as an indicator of a defined pretension of the clamping element.

In another embodiment, within the contoured body at the opposite angled portions there can be arranged two snap-in locking elements which are directed towards each other and can be brought into engagement with each other, preferably an undercut element and a catch element, by means of which the angled portions can be connected in a pretensioned position of the clamping element in a snap-in locking manner, wherein said snap-lock connection can be released or disengaged again. Thus, the clamping element can be locked in a predefined pretension in a particularly user-friendly manner prior to the surgical operation. After the fastening, the snap-lock connection can be released or disengaged so that there will exist a tractive force between the fixing means which corresponds to the pretension.

Furthermore, the setting or fixation device according to the invention can also comprise at least one clamping sleeve in which a fixing means can be received, wherein the clamping sleeve preferably comprises two cranks at the end faces thereof, which are spaced apart from each other substantially in correspondence with the height of a wall of the clamping element. The cranks at the end faces of the clamping sleeve prevent a displacement of the clamping element in the axial direction. Moreover, the clamping sleeve has a larger peripheral area than e.g. a threaded portion of a fixing means, whereby the area of contact between the fixing means and the clamping element is increased and a corresponding point load is reduced. Consequently, a potential abrasion of the material and an associated contamination of the surrounding body tissue can be minimized.

The clamping sleeve according to the invention can be designed in two parts and can be joinable together in the axial direction so that the wall of the clamping element can be clamped between the cranks. In doing so, a firm seat between the fixing means and the clamping element is created, and, furthermore, it is avoided that body tissue finds its way in between or gets jammed in between or grows into between said two elements.

The healing process of a bone fracture can further be assisted when the supporting cortical layer of the bone will be subjected to loads again after a certain time in order to regain again a load-bearing function, as is for instance also the case after the removal of a plaster splinting. In case of a conventional setting, however, a part of the load-bearing function will permanently be taken over by the rigid bone plate.

According to one aspect of the invention, the setting device can comprise elements made of an absorbable synthetic material, i.e. of a material which will be decomposed by the surrounding body tissue. Absorbable synthetic materials have, however, relatively brittle material properties. Consequently, they are only suitable to a limited extent for the formation of regions which are exposed to mechanical stresses. Furthermore, such materials are also not intended for the formation of resilient bodies.

Accordingly, in a further embodiment, the clamping sleeve can be divided radially into two sections, wherein the radially inner section or the radially outer section is made of an absorbable synthetic material. By the absorption of one of the two sections, a clearance is created between the fixing means and the clamping element which results in a force decoupling between the fixing means. If, preferably, an outer section consists of a metal and an inner section consists of an absorbable synthetic material, there still remains a local limitation of the clamping element by means of the cranks of the outer section. Thereby, a detaching of the clamping element from its installation or a potential impairment or damaging of the adjacent body tissue can be prevented.

Alternatively, in a further embodiment, the setting device can comprise at least one sleeve element which is made of an absorbable synthetic material, wherein the fixing means can be received within the sleeve element. By the absorption of the sleeve element, in the setting device there is also created a force decoupling between the fixing means as mentioned above. Therefore, the force transmission between the setting device and the bone gets lost with the progressing absorption of the sleeve elements, whereby the strains on the bones are increased again.

On the other hand, in another embodiment of the setting or fixation device, between the angled portions an inlay can be wedged, the length of which presses apart the angled portions against a pretension of the clamping element, wherein the inlay consists of an absorbable material. The inlay holds the clamping element under a pretension. When the inlay is absorbed during the healing process, the clamping element returns to its initial position, wherein the distance between the receiving portions is again increased and a force transmission between the fixing means with respect to a tractive force vanishes.

According to an exemplary embodiment, adjacent clamping elements can overlap each other in the setting or fixation device such that the fixing means, the clamping sleeve or the sleeve element can be enclosed by the receiving portions at the end faces of the overlapping clamping elements. Thus, setting devices can be realized with a chain-shaped or a star-shaped arrangement of clamping elements. By a chain arrangement, a compression between several bone fragments can be obtained with a low number of fixing means, or a bridging of longer distances can be achieved with a smaller width dimension of the clamping element. By a star-shaped arrangement of clamping elements, a multidirectional compression can be applied onto bone fragments with intersecting fracture lines, as for instance in case of a comminuted fracture and in particular a wedge fracture. By the selection of the arrangement of clamping elements and of the connection points, the setting device can be aligned individually to the course of different fracture margins.

In particular in one embodiment, an inner radius of the receiving portions at the end faces of the clamping element can correspond to the outer radius of a peripheral area section of a fixing means, of a sleeve element or of a clamping sleeve. By a contact area which is as large as possible between the inner radius of curvature of the clamping element and the outer radius of the fixing means, the point load between the elements can be reduced. As described above, this results in a minimization of a potential contamination of the surrounding body tissue by a material abrasion. Furthermore, due to the tensile stress, a secure seat or fit of the fixing means at the clamping body does not require any enclosing reception element. Consequently, the necessity of reception bores or of any other enclosing reception elements is abolished in favour of a simple design of the clamping element.

According to the invention, the clamping element can be manufactured from a selected hollow profile or a selected, substantially hollow profile which is extruded. The clamping element is formed by a hollow-profile section which is cut off at a cross-section predetermined in the longitudinal direction of the hollow profile and forming the height of the clamping element. Additionally, cutaway portions or openings can be cut into the wall of the hollow-profile section. In this manner, the clamping element can be manufactured with a particularly small effort. The ratio of the height to the wall thickness offers a possibility to choose the elasticity and the rigidity with respect to the plane of extension of the contour of the clamping element.

Optionally, the clamping element can be manufactured from a selected solid profile which is cast by means of extrusion molding. The clamping element is formed by a solid-profile section which is cut off at a cross-section predetermined in the longitudinal direction of the solid profile and forming the height of the clamping element. Then the solid material is machined in order to form a closed contoured body which has a substantially hollow cross-section and is enclosed by a peripheral wall. Additionally, cutaway portions or openings can be cut into the wall of the closed contoured body. In this manner, special designs of the clamping element can be produced with a relatively small expenditure.

BRIEF DESCRIPTION OF THE DRAWINGS

Further embodiments, features, and advantages of the invention will become apparent from the following description of embodiments which is made under reference to the accompanying figures, wherein.

DETAILED DESCRIPTION OF THE INVENTION

Figure 1:
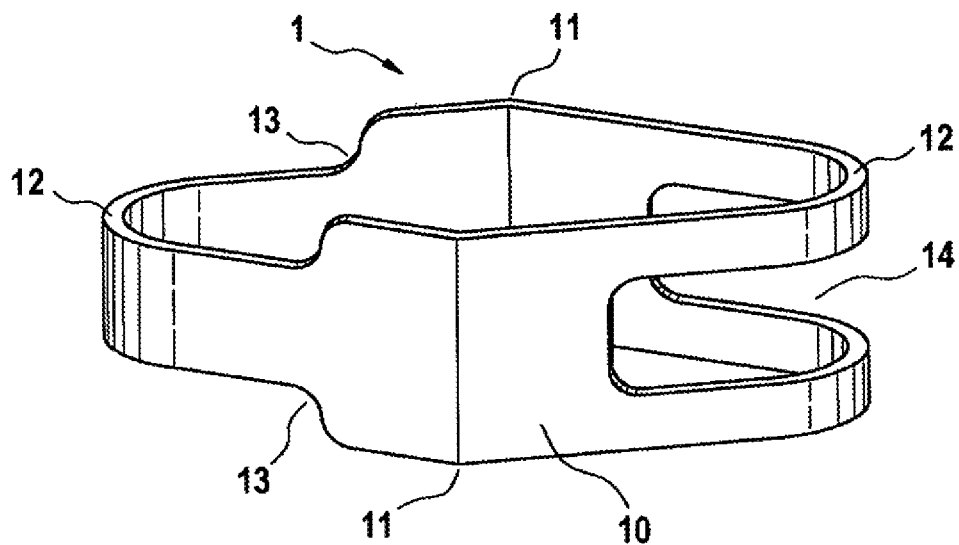
FIG. 1 is a perspective view of a clamping element according to the invention.

FIG. 1 shows a clamping element 1 with a peripheral wall 10 which comprises two angled portions 11 and two receiving portions 12. The two receiving portions 12 are arranged opposite to each other at the end faces of the clamping element 1, i.e. in a longitudinal direction between two fixing means (not shown), and have a curvature which points outwards. The two angled portions 11 lie opposite to each other at the lateral flanks of the clamping element 1 in a width direction, i.e. perpendicular to the longitudinal direction, and have a curvature which points outwards. The clamping element 1 as shown in FIG. 1 is substantially of a rhomboidal form.

When the radius of curvature of the angled portions 11 extends over the entire length thereof, the clamping element 1 can also have a substantially oval shape.

Here, the radius of curvature of the receiving portions 12 is for instance chosen such that it corresponds to a fixing means or a clamping sleeve or, if applicable, to a sleeve element, and receives it along the surface. Thus, due to the applying tensile stress, a reception of the fixing means or of the clamping sleeve with a positive fit is guaranteed.

The clamping element 1 can comprise a peripheral wall with a uniform thickness. Among other things, said design enables a manufacture of the clamping element 1 by the bending of a metal strip loop to be joined by means of a welding seam or by the re-forming of a profile having a welding seam.

The upper and lower edges of the wall are rounded or chamfered in order to minimize an irritation of the surrounding body tissue.

Furthermore, the wall 10 of the clamping element 1 can have a uniform height so that the clamping element 1 can be cut off from a profile, for instance an extrusion profile, in the form of a profile section via a cross-section. This can be carried out in a particularly cost-effective manner with a hollow profile with a suitable contour and wall thickness, as here only the wall height has to be determined by specifying the cross-section for the cutting-off. Additionally, the clamping element 1 can be manufactured by machining from a solid-profile section in order to form further structures, as for instance coupling elements or limiting bars, in an integral and individual manner.

The clamping element 1 is manufactured from biocompatible materials. Additionally, also a hybrid structure is possible in which the wall of the angled portions 11 consists of a material with the desired resilient property, and in which further sections of the clamping element 1, as e.g. the receiving portions 12, are formed of a rigid or absorbable material. A hybrid structure can also be produced according to anyone of the above-mentioned methods, in particular by the selection of a corresponding composite profile which, when viewed from the cross-sectional point of view, is composed of sections of different materials.

As a basic material for the clamping element 1, for instance metals from the group consisting of: X42CrMo15, X100CrMo17, X2CrNiMnMoNNb21-16-5-3, X20Cr13, X15Cr13, X30Cr13, X46Cr13, X17CrNi16-2, X14CrMoS17, X30CrMoN15-1, X65CrMo 17-3, X55CrMo14, X90CrMoV18, X50CrMoV15, X 38CrMo V15, G-X 20CrMo13, X39CrMo17-1, X40CrMoVN16-2, X105CrMo17, X20CrNiMoS13-1, X5CrNi18-0, X8CrNiS18-9, X2CrNi19-11, X2CrNi18-9, X10CrNi18-8, X5CrNiMo17-12-2, X2CrNiMo17-12-2, X2CrNiMoN25-7-4, X2CrNiMoN17-13-3, X2CrNiMo17-12-3, X2CrNiMo18-14-3, X2CrNiMo18-15-3; X 2 CrNiMo 18 14 3, X13CrMnMoN18-14-3, X2CrNiMoN22136, X2CrNiMnMoNbN21-9-4-3, X4CrNiMnMo21-9-4, X105CrCoMo18-2, X6CrNiTi18-10, X5CrNiCuNb16-4, X3CrNiCuTiNb12-9, X3CrNiCuTiNb12-9, X7CrNiAl17-7, CoCr20Ni15Mo, G-CoCr29Mo, CoCr20W15Ni, Co-20Cr-15W-10Ni, CoCr28MoNi, CoNi35Cr20Mo10, Ti1, Ti2, Ti3, Ti4, Ti-5Al-2,5Fe, Ti-5Al-2,5Sn, Ti-6Al-4V, Ti-6Al-4V ELI, Ti-3Al-2,5V (Gr9), 99,5Ti, Ti-12Mo-6Zr-2Fe, Ti-13, 4Al-29Nb, Ti-13Nb-13Zr, Ti-15Al, Ti-15Mo, Ti-15Mo-5Zr-3Al, Ti-15Sn, Ti-15Zr-4Nb, Ti-15Zr-4Nb-4Ta, Ti-15Zr-4Nb-4Ta-0,2Pd, Ti-29Nb-13Ta-4,6Zr, Ti-30Nb-10Ta-5Zr, Ti-35,5Nb-1,5Ta-7,1Zr, Ti-35Zr-10Nb, Ti-45Nb, Ti-30Nb, Ti-30Ta, Ti-6Mn, Ti-5Zr-3Sn-5Mo-15Nb, Ti-3Al-8V-6Cr-4Zr-4Mo, Ti-6Al-2Nb-1Ta-0,8Mo, Ti-6Al-4Fe, Ti-6Al-4Nb, Ti-6Al-6Nb-1Ta, Ti-6Al-7Nb, Ti-6Al-4Zr-2Sn-2Mo, Ti-8, 4Al-15,4Nb, Ti-8Al-7Nb, Ti-8Al-1Mo-1V, Ti-11Mo-6Zr-4Sn, can be used.

Furthermore, polymers from the group consisting of: MBS, PMMI, MABS, CA, CTA, CAB, CAP, COC, PCT, PCTA, PCTG, EVA, EVAL, PTFE, ePTFE, PCTFE, PVDF, PVF, ETFE, ECTFE, FEP, PFA, LCP, PMMA, PMP, PHEMA, Polyamide 66, Polyamide 6, Polyamide 11, Polyamide 2, PAEK, PEEK, PB, PC, PPC, PETP, PBT, MDPE, LDPE, HDPE, UHMWPE, LLDPE, PI, PAI, PEI, PIB, POM, PPO, PPE, PPS, PP, PS, PSU, PESU, PVC, PVC-P, PVC-U, ABS, SAN, TPE-U, TPE-A, TPE-E, PVDC, PVA, SI, PDMS, EPM, EP, UF, MF, PF, PUR, UP, PEBA, PHB, PLA, PLLA, PDLA, PDLLA, PGL, PGLA, PGLLA, PGDLLA, PGL-co-poly TMC, PGL-co-PCL, PDS, PVAL, PCL, Poly-TMC, PUR (linear), NiTi Superelastic, NiTi Shape Memory, can be used.

Furthermore, also ceramics from the group consisting of: $Al_2O_3$ (alumina oxide), Y-TZP (zirconium oxide ceramic), AMC (alumina matrix composite), HA (hydroxyl apatite), TCP (tricalcium phosphate), Ceravital (glass ceramic/Bioglas®), FZM/K (zirconium oxide, partially stabilized), TZP-A (zirconium oxide ceramic), ATZ (alumina-toughened zirconia), C799 (alumina oxide ceramic), Schott 8625 (transponder glass), can be used.

Furthermore, also any combinations thereof can be used.

The rhomboidal shape for the clamping element 1 as represented in FIG. 1 has favourable properties with regard to the longitudinal expansion and the transverse contraction of the clamping element 1, since a resilient behaviour in the longitudinal direction of the clamping element 1 can be predetermined by the height-width ratio of the wall sections extending in parallel with respect to one another.

When a rhomboidal clamping element 1 is extended, or in case of a pressure on the angled portions 11 acting in opposite direction, there applies approximately a relationship or ratio between the longitudinal expansion and the transverse contraction of:

$$\Delta l = \sqrt{4x^2 - (b - \Delta b)^2} - \sqrt{4x^2 - b^2}$$

wherein b is the width of the clamping element 1 in the initial position; $\Delta b$ is the negative change in length in the width direction; $\Delta l$ is the positive change in length in the longitudinal direction; and x is the distance between the curvature apex of a receiving portion 12 and the curvature apex of an angled portion 11, said distance remaining approximately constant.

Furthermore, the resilient behaviour of the clamping element 1 can be influenced by an appropriate selection of the wall cross-section and of the material. Here, the resilient behaviour depends on the material-specific modulus of elasticity (Young's Modulus) and on the specific inner material friction of the chosen material.

By taking into consideration of the inner material friction which remains after the removal of a pretensioning force, consequently, approximately a tractive force of:

$$Fl = \frac{Fb}{k} - Ffric$$

exists, wherein Fl is the tractive force in the longitudinal direction; Fb is the applied pretensioning force in the width direction; Ffric is the specific inner material friction; and k is a spring constant (modulus of resilience) with respect to the material-specific modulus of elasticity and to the geometry.

Figure 2:
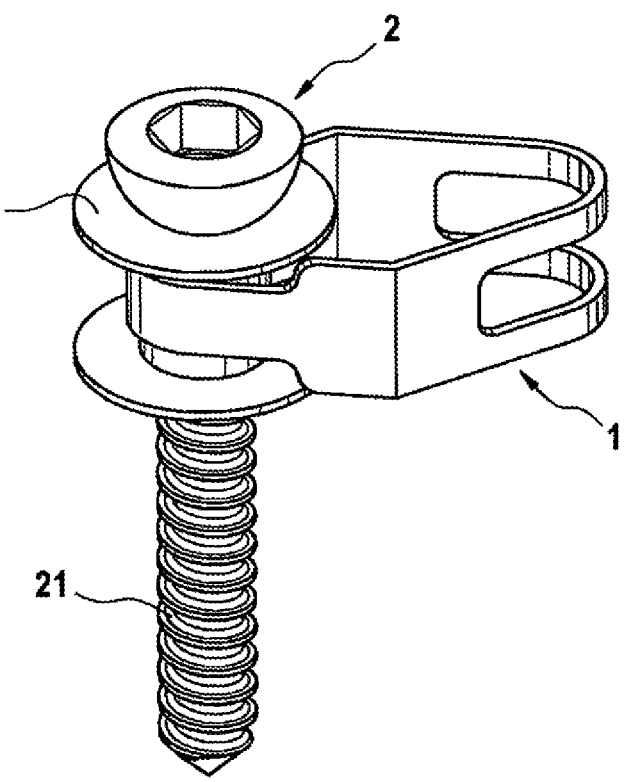
FIG. 2 is a perspective view of a clamping element and of a cortical screw with a clamping sleeve as a fixing means.

As can be inferred from FIG. 2, the setting or fixation device also comprises a fixing means 2 in addition to the clamping element 1. The fixing means 2 can be a surgical implant, as for instance a bone nail, a bone screw and in particular a cortical screw 21, which is placed into the bone. In this connection, the thickness of the corticalis of the different bones differs substantially according to the bones, for instance at a thigh bone or a jaw bone. There are available cortical screws 21 with staggered diameters and lengths for the various applications, which are standardized according to ISO 5835: 1991 or ASTM: F 543-07.

Principally, in this connection there are not given any fixed specifications between the size of the clamping element 1 and the respective bone, though a proportional dimensioning of the clamping element 1 with respect to the used screw system is conceivable. From the practical medical technology there can be approximately established a connection between the nominal diameter of the cortical or spongiosa screw and the field of application, which is listed in the following table:

| Screw System | Field of Application |
| --- | --- |
| HA 1.5 Cortical | oral and maxillofacial surgery |
| HA 2.0 Cortical | cranio; foot surgery; hand surgery |
| HA 2.5 Cortical | cranio; foot surgery; trauma |
| HA 3.5 Cortical | thorax; lower back; arm surgery |
| HA 4.0 Cortical | thorax; spinal column; hip and pelvis area |
| HA 4.5 Cortical | leg surgery; trunk; fibula; shoulder |
| HA 5.0 Cortical | leg surgery; tibia; femur |
| HB 4.0 Spongiosa | depending on the load case |
| HB 6.0 Spongiosa | depending on the load case |

The selection of the dimensioning and positioning of the screw system as well as of the clamping element 1 also depends on the type of fracture (e.g. transverse fracture, oblique fracture) and on the location of a fracture, from which there will result different load cases.

Thus, in case of diaphyseal fractures, in most cases cortical systems will be used, as here no spongiosa portion is given. On the other hand, in case of fractures near a joint very often spongiosa systems will be used, as the percentage of the spongiosa is very high in this area. Spongiosa screws have a higher percentage contact area, as they have a larger core diameter for the same nominal diameter. In case of joint fractures, i.e. fractures with the participation of the articular surface, there will be used cortical screw systems as well as spongiosa systems in dependence on the local anatomic conditions. In case of a multifold fracture, also both systems can be used.

Furthermore, apart from a single, i.e. monocortical fixation possibility, also bicortical systems can be provided in which the screw is fixed through the bone in both cortical regions.

The use of the clamping element 1 for setting a fracture site can be carried out in particular as described in the following.

The angled portions 11 of the clamping element 1 will be pressed from the outside, whereby the clamping element 1 experiences a transverse contraction. In this connection, a longitudinal expansion of the clamping element 1 occurs, i.e. the distance between the receiving portions 12 increases. Then two fixing means, for instance cortical screws, will be pushed through so that with the increased distance between the receiving portions 12 they will rest against the inner surface thereof. In this position, the fixing means will be inserted into opposite fracture ends of a bone. Due to the fixing means, the clamping element 1 will be held in the longitudinally extended shape, i.e. under a pretension, after the removal of the external force. Said pretension permanently exerts a tractive force between the fixing means. The tractive force between the fixing means will be used in the setting device for the adaption of the ends of a fracture in a bone fracture.

Furthermore, in the clamping element 1 as represented in FIG. 1, a kind of a tongue is formed by an upper and lower cutaway portion 13 in a wall section in the region of a receiving portion 12. Complementary thereto, in the region of the opposite receiving portion 12 there is formed a kind of a groove in a wall section by a central opening 14. The tongue structure and the groove structure can be fit into each other so that the contours of the walls 10 of two adjacent clamping elements 1 can overlap each other. The cutaway portions 13 and the openings 14 extend in the longitudinal direction of the clamping element 1 to such an extent that in the overlapping area of two or more clamping elements 1 the same fixing means 2 or the same clamping sleeve can be completely enclosed by the receiving portions 12 of the clamping element 1. Hence, different clamping elements 1 can be combined with each other according to the principle of a modular construction system.

Furthermore, the fixing means 2 can comprise a section with a clamping sleeve 20. Upwards and downwards, the clamping sleeve 20 comprises a crank at the end faces thereof, said crank preventing a movement of the clamping element 1 in the axial direction of the fixing means 2. The clamping sleeve 20 is for instance formed separately and will be combined with a cortical screw 21 which is received in a through-hole of the clamping sleeve 20.

Figure 3:
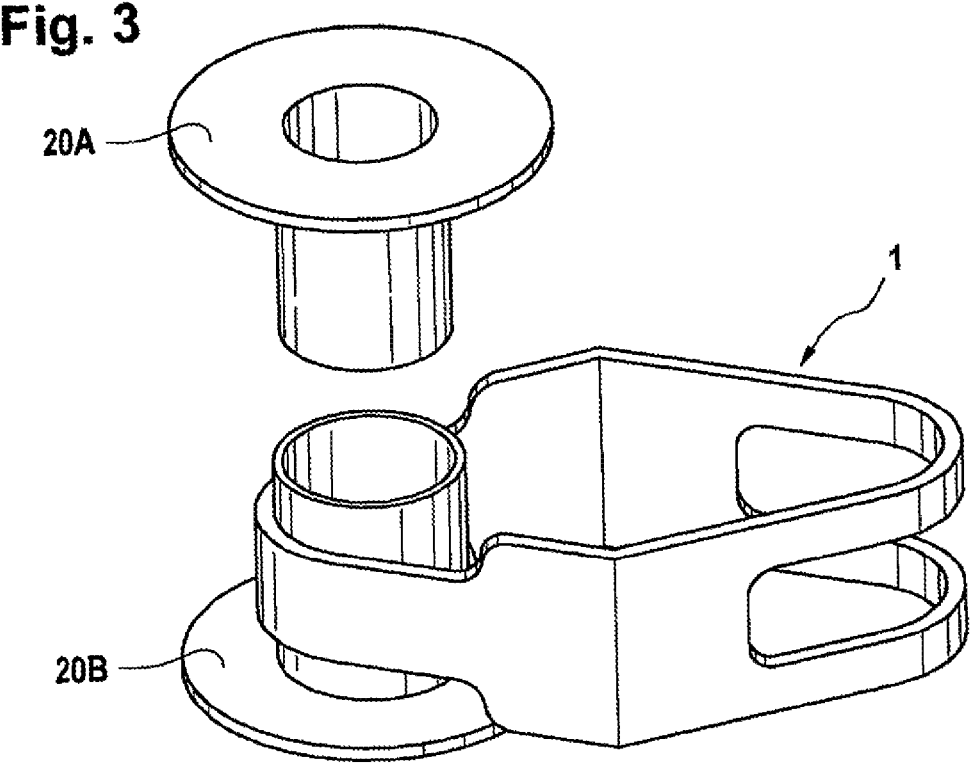
FIG. 3 is a perspective view of a clamping element and of a two-part clamping sleeve.

In the embodiment in FIG. 3, the clamping sleeve 20 is formed in two parts, wherein the two halves 20A and 20B of the clamping sleeve 20 will be joined together in the axial direction of the fixing means 2. Consequently, a wall section of the clamping element 1 can be wedged in between the cranks at the end faces of the halves 20A and 20B of the clamping sleeve 20.

Figure 4:
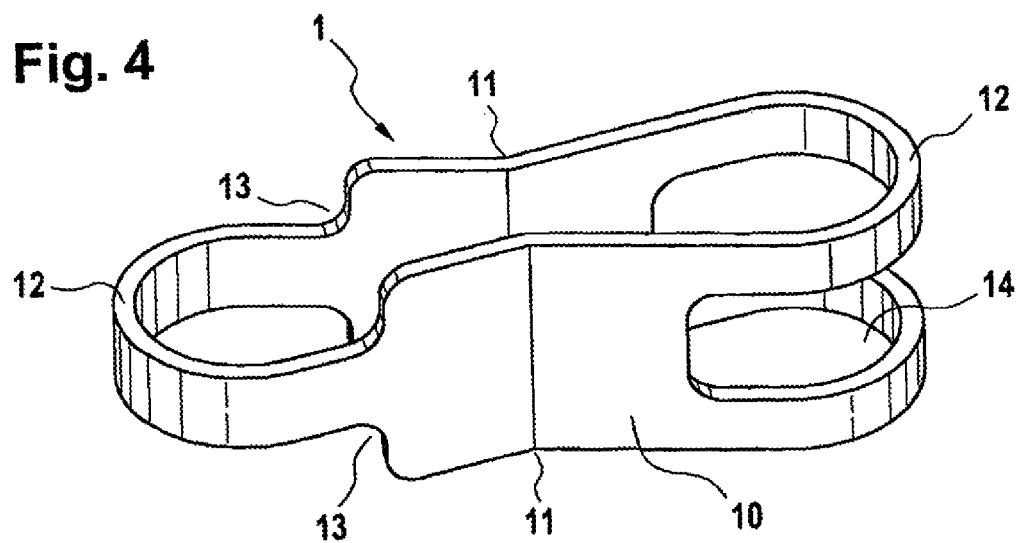
FIG. 4 is a perspective view of a spectacles-shaped clamping element.

The clamping element 1 as depicted in FIG. 4 comprises two inwardly pointing angled portions 11. In this case, a longitudinal expansion for the pretensioning of the clamping element 1 is achieved by a pressing apart of the angled portions 11. The remaining functioning is similar to the one of the clamping element 1 as described above in FIG. 1.

Figure 5:
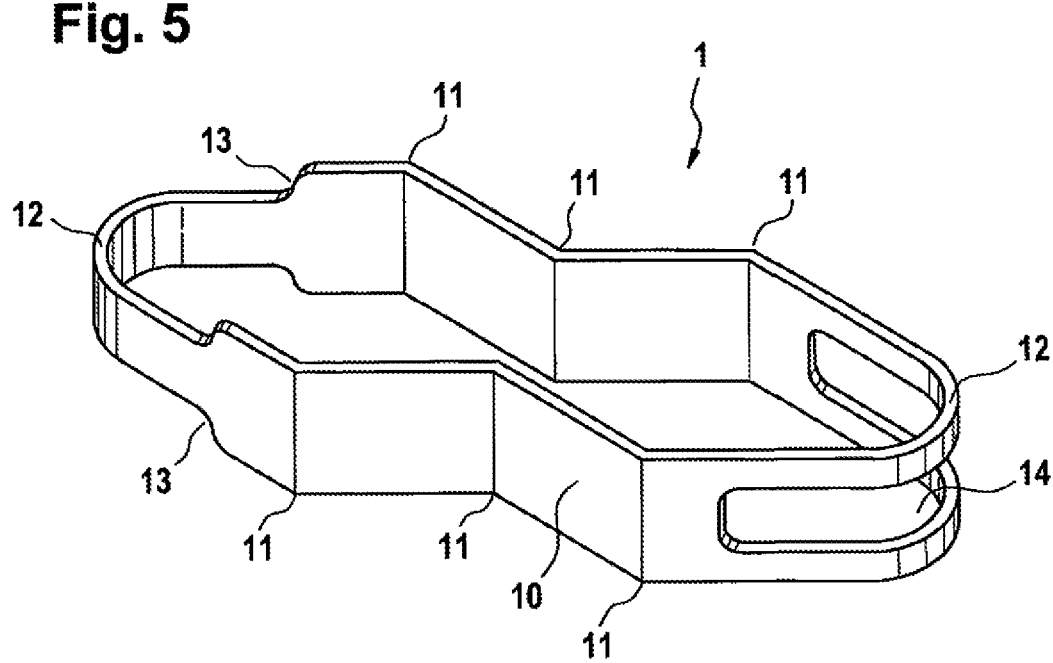
FIG. 5 is a perspective view of a double-rhomboidal clamping element.

From FIG. 5 there can be inferred a clamping element 1 which comprises three alternating angled portions 11, respectively, at the lateral flanks. By the combination of several identical angles of curvature, a pretension adds up over the individual angled portions 11 to an entire longitudinal expansion of the clamping element 1. Thus, e.g. with the same modulus of elasticity, wall cross-section and angle of curvature, a narrower or longer design of the clamping element 1 is realizable without substantially changing the resilient behaviour in the longitudinal direction of the clamping element 1. The further handling and functioning correspond substantially to those of the embodiments shown in FIG. 1 and FIG. 4.

Figure 6:
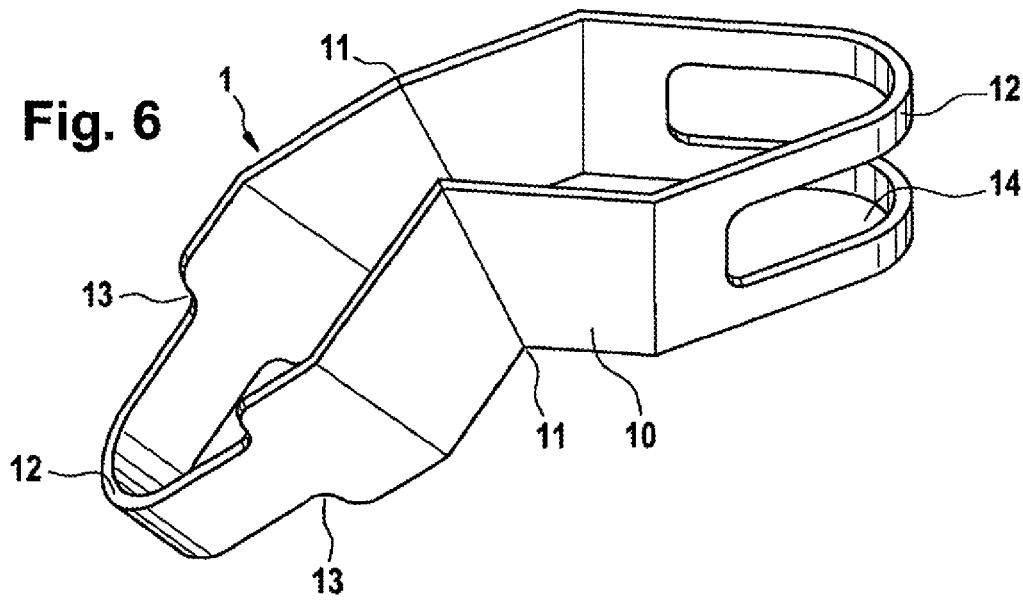
FIG. 6 is a perspective view of a clamping element which has a curvature in the plane of extension of the contour.

The clamping element 1 in FIG. 6 has a curvature in the plane of extension of the contour and, thus, represents one of several alternative designs for an anatomic adaptation. The clamping element 1 can also be curved with respect to one or several random axes or points. The anatomic adaptations can refer to deformations in the plane of extension of the contour as well as also to the height of the wall of the clamping element 1.

Figure 7:
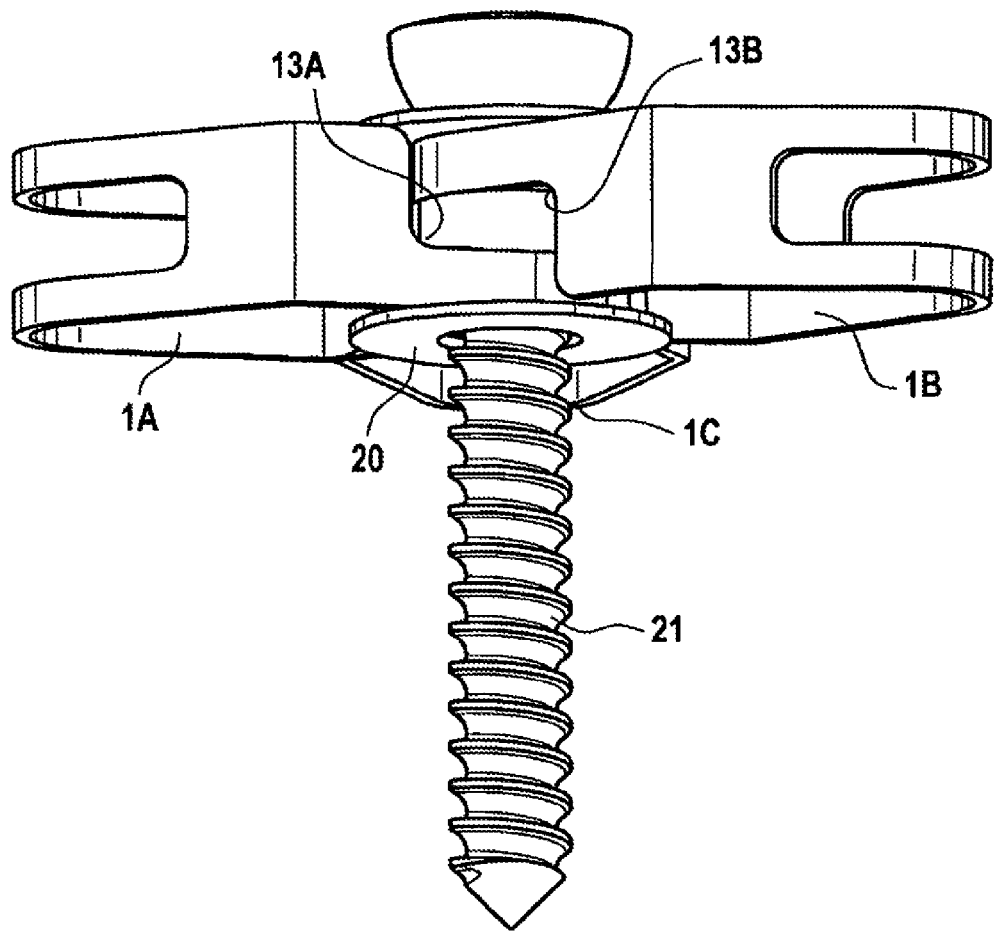
FIG. 7 is a detailed view of a combination with overlapping clamping elements.

As can be inferred from FIG. 7, a cutaway portion 13 in the wall 10 can also be arranged offset with respect to the wall height. In the illustrated embodiment of a combination, three tongues of the clamping elements 1A-C overlap each other and enclose the same clamping sleeve 20, wherein the tongue structures extend flush with the upper side or lower side of the clamping elements 1A and 1B. The clamping elements 1A and 1B can be identical, wherein one of the two is arranged in a reversed manner. The tongue of the clamping element 1C extends centrally to the wall height and is received between the tongues of the clamping elements 1A and 1B.

The stack arrangement as shown in FIG. 7 consists of superimposed tongue structures of the clamping elements 1A-C and, consequently, does not comprise any groove.

There can, however, also be realized embodiments of connection points with a random number and combination of tongue structures with or without a groove. Advantageously, the height and the position of the respective tongue structures and groove structures are formed in dependence on the number of the overlapping clamping elements 1 such that they mutually complement each other in the overlapping area to a stack height which corresponds to the height of a clamping element 1.

Figure 8:
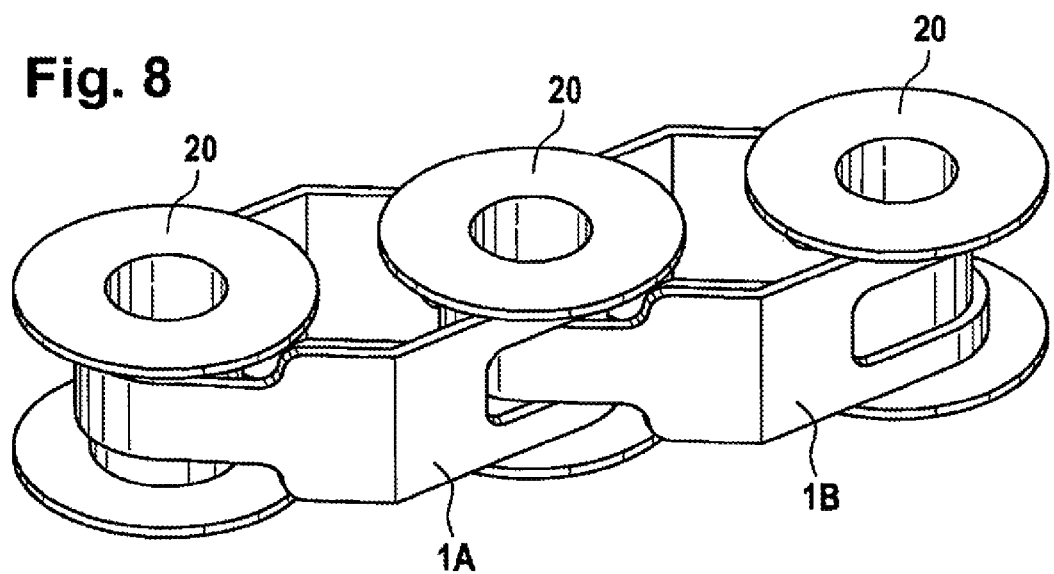
FIG. 8 is a perspective view of a setting or fixation device realized as a chain arrangement.

In order to bridge longer distances, several clamping elements 1 can be arranged in a chain. As is illustrated in FIG. 8, for said embodiment preferably clamping elements 1 with a tongue structure on the one hand and a complementary groove structure on the other hand are provided. A chain arrangement can, however, also be realized by an overlapping of two reversed tongue structures.

For the connection thereof, the clamping elements can enclose just a clamping sleeve 20, i.e. without a cortical screw 21 or the like. Thus, the tractive force of the pretensioned clamping elements 1 of a chain arrangement can for instance be active between two fixing means at the two ends of the chain arrangement. In this embodiment, a two-part clamping sleeve 20 is provided, the two halves 20A and 10B of which are for instance connected by means of a press fit.

Figure 9:
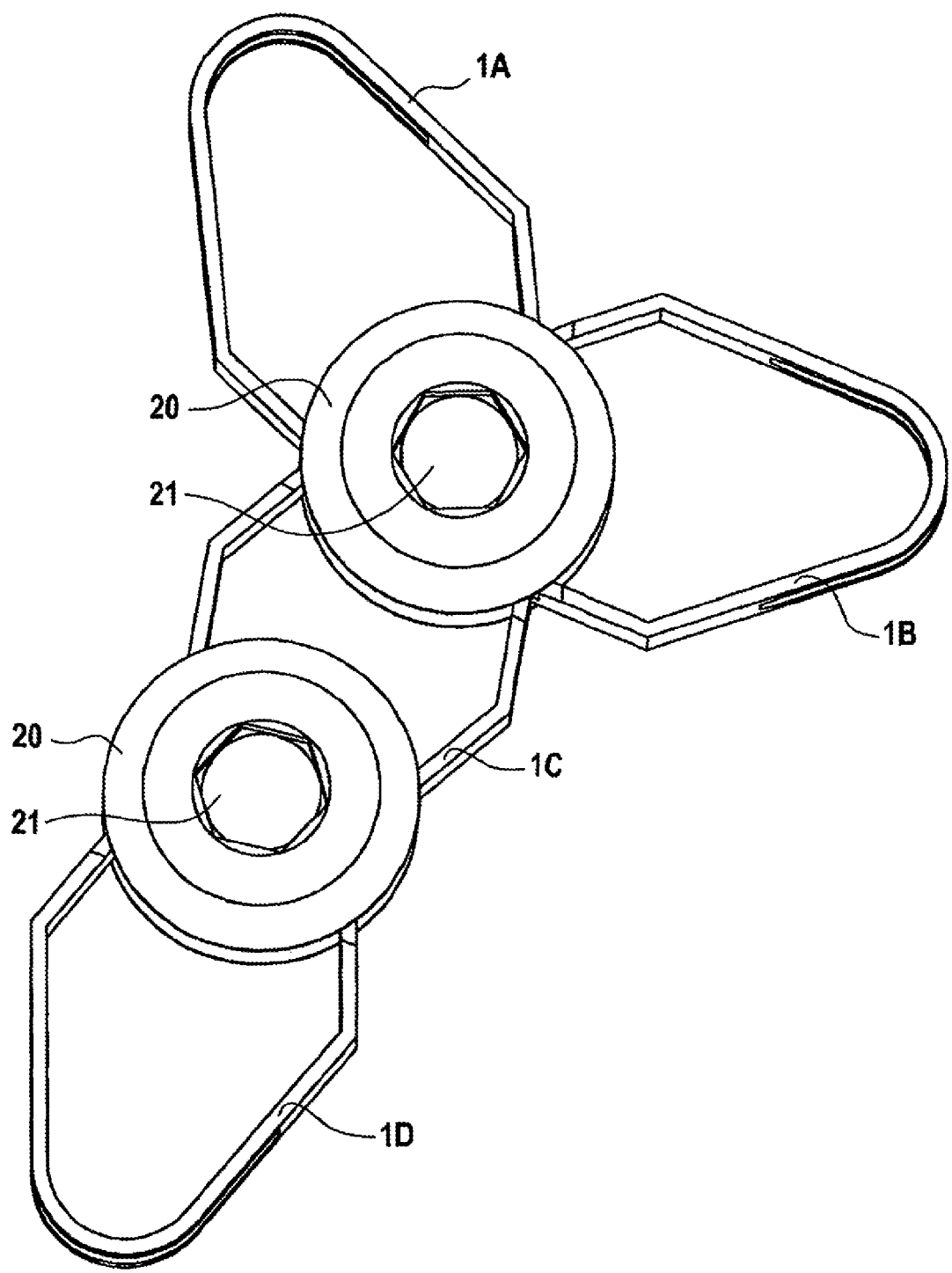
FIG. 9 is a perspective view of a setting or fixation device realized as a star-shaped arrangement.

With the modular structure of the present setting or fixation device, also a star-shaped arrangement or any random combination of chain-shaped and star-shaped arrangements can be realized, as is shown in FIG. 9. Depending on the angle of curvature of the receiving portions 12 and on the width of the overlapping clamping elements 1, there can be formed a star-shaped arrangement of three or more clamping elements 1. Also in this combination, a clamping sleeve 20 with or without an inserted cortical screw 21 or the like can be enclosed by the clamping elements 1.

Figure 10A:
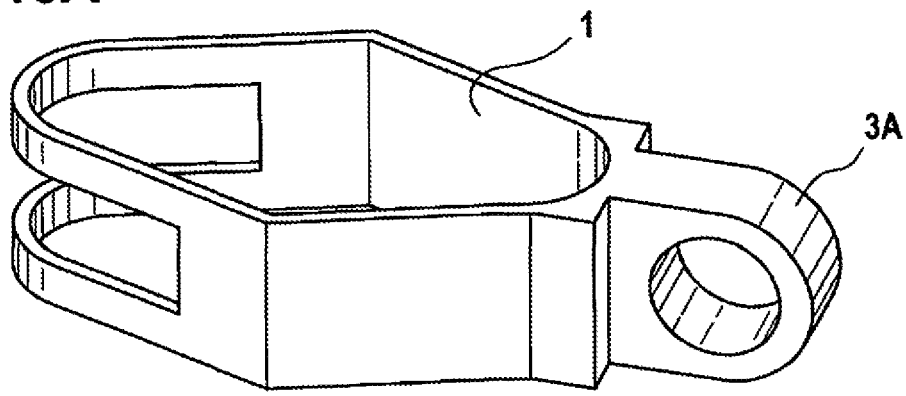
FIGS. 10 A-C are perspective views of clamping elements with coupling elements.
Figure 10B:
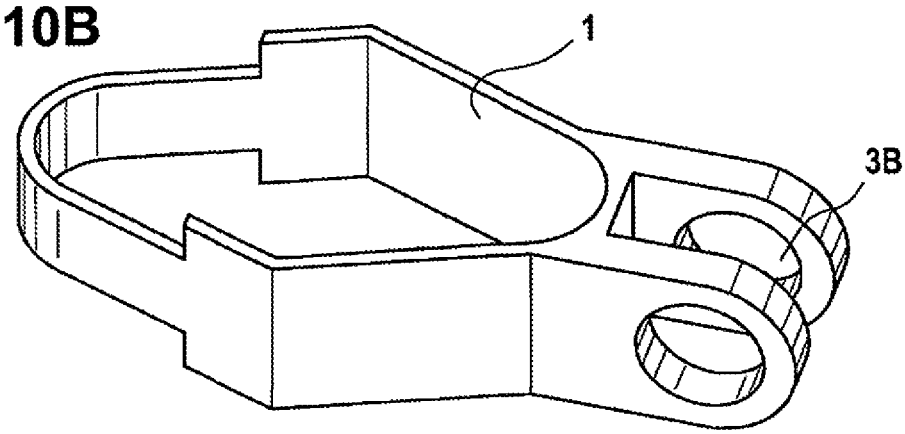
Figure 10C:
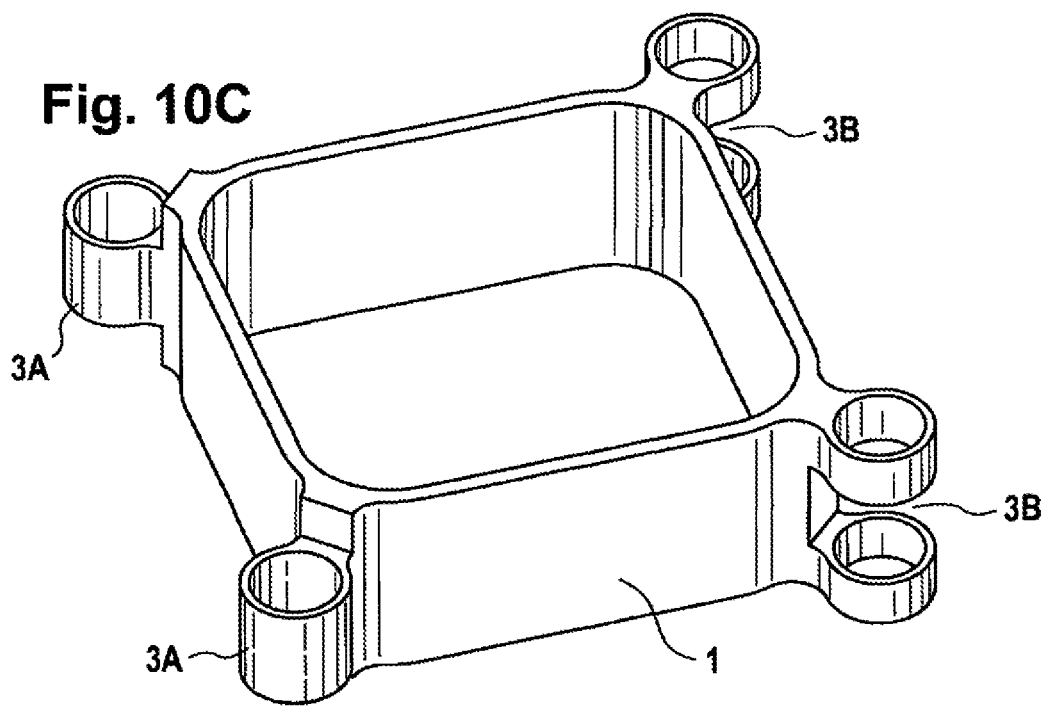

A combination of adjacent clamping elements 1 can also be established via coupling elements 3A and 3B which are formed at the outer surface of the wall 10. To this end, the coupling elements can have the shape of an eyelet or a double eyelet with a receiving gap, which can also be joined together in the sense of a tongue and groove connection. Here, the distance of the receiving gap in the coupling element 3B advantageously corresponds to the thickness of the coupling element 3A. The eyelet-shaped coupling elements 3A and 3B also comprise a hole through which, in the assembled state, they can be penetrated by a bolt, a screw or the like. The hole of the coupling elements 3A and 3B can, as is shown in FIG. 10 A and FIG. 10 B, extend in the width direction of the clamping element 1, or, as is shown in FIG. 10 C, can extend perpendicularly to the plane of extension of the contour, or can extend in any other direction.

Figure 11C:
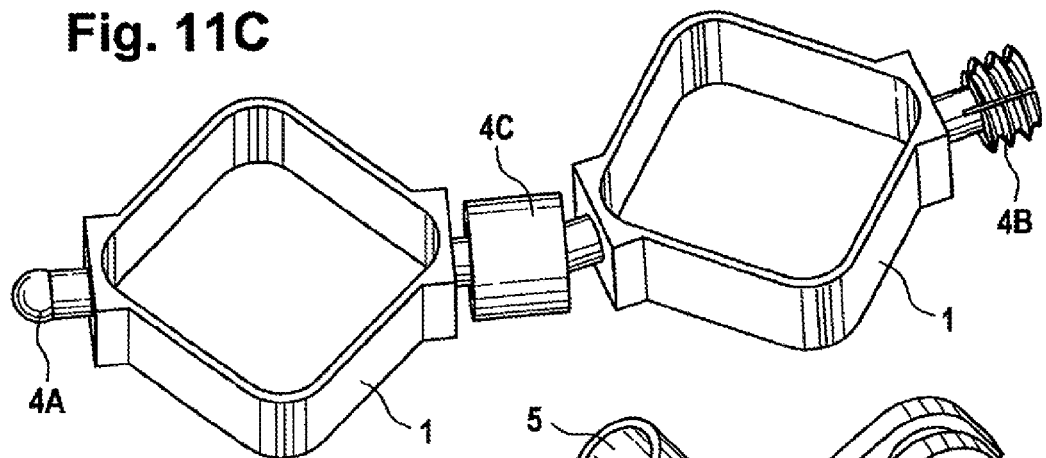
FIGS. 11 A-C are perspective views of a clamping element with a clamping connection in the form of a ball joint.

As can be inferred from FIG. 11A to C, the clamping elements 1 can also be connected by means of a clamping connection in the form of a ball joint. Therefor there is formed a ball element 4A and/or a spherical clamping part 4B at the outer surface of the wall 10 of the clamping element 1. The clamping part 4B comprises a spherical inner surface with expansion gaps and a male thread at which it can be clamped by means of a nut 4C. When the ball element 4A is pressed into the clamping part 4B with the aid of the extension gaps, the clamping part 4B can optionally be set under a tension or can be locked by a threaded nut on the outer surface to such an extent that the slipping out of the ball element 5B is prevented or that the connection is fixed with regard to position.

Figure 12A:
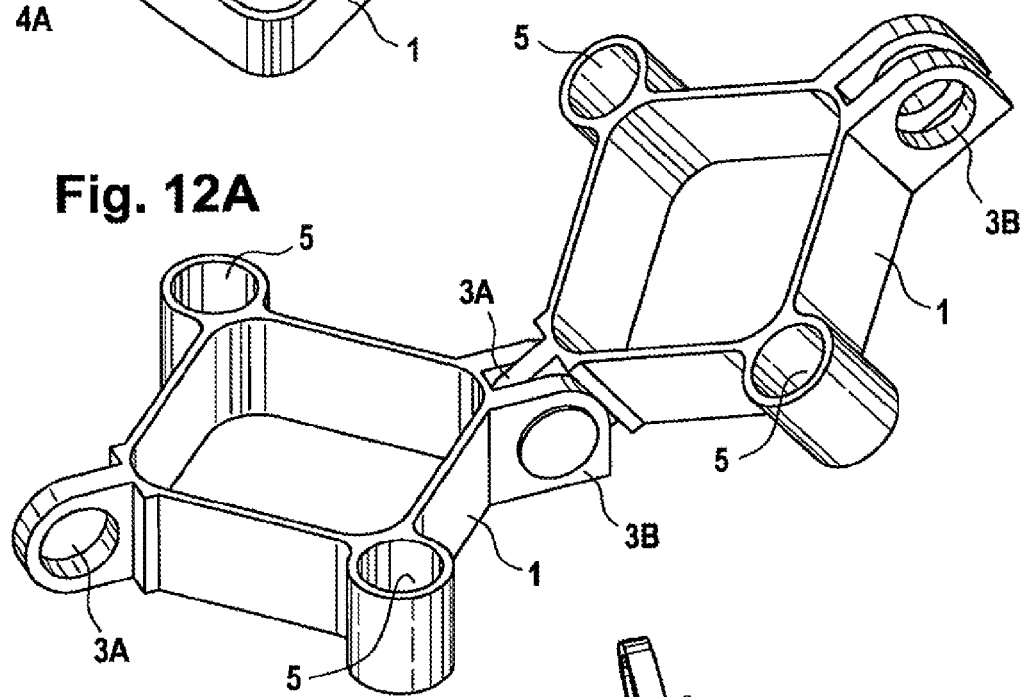
FIGS. 12 A-B are perspective views of clamping elements with fastening eyes.
Figure 12B:
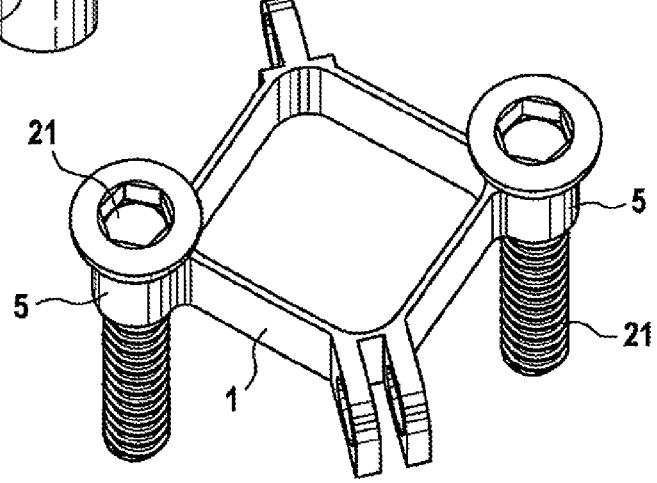

As is shown in FIGS. 12 A and 12 B, a clamping element 1 can alternatively be connected at a bone via fastening eyes in which a cortical screw or the like is received. In this case, no clamping sleeve 20 is required. The fastening eyes are formed at the outer surface of the wall 10 of the clamping element 1.

Figure 13:
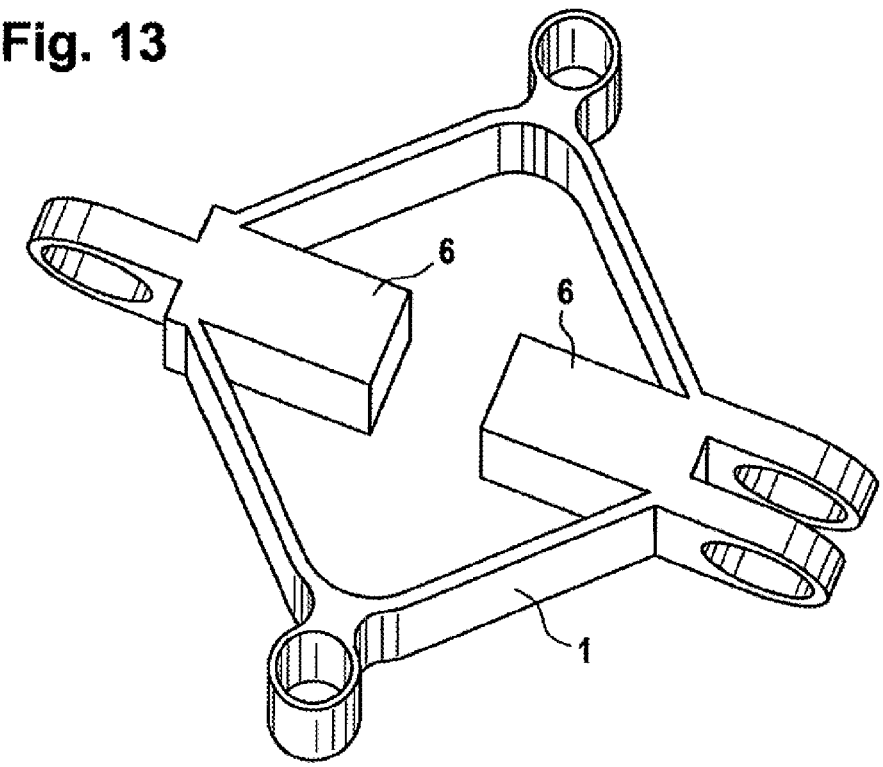
FIG. 13 is a perspective view of a clamping element with limiting bars.

As is shown in FIG. 13, limiting bars 6 can be formed in a clamping element 1 at two opposing wall portions, said limiting bars 6 extending from the inner surface of the wall 10 of the clamping element 1 to the center thereof. When the clamping element 1 is elastically deformed due to a force introduced from the outside, the ends of the limiting bars 6 move towards each other. The resilient behavior stops when the ends of the limiting bars 6 come into contact with each other, whereby a further deformation path of the clamping element 1 is blocked.

The limitation of the deformation path offers a protective function against permanent deformations. Furthermore, when the clamping element 1 is squeezed, a defined pretension can be obtained by means of the limiting bars 6. Said property can be used advantageously in particular when the clamping element 1 is inserted during a surgical operation or in advance for a dimensioning of connections of several clamping elements 1 of a setting device.

Figure 14:
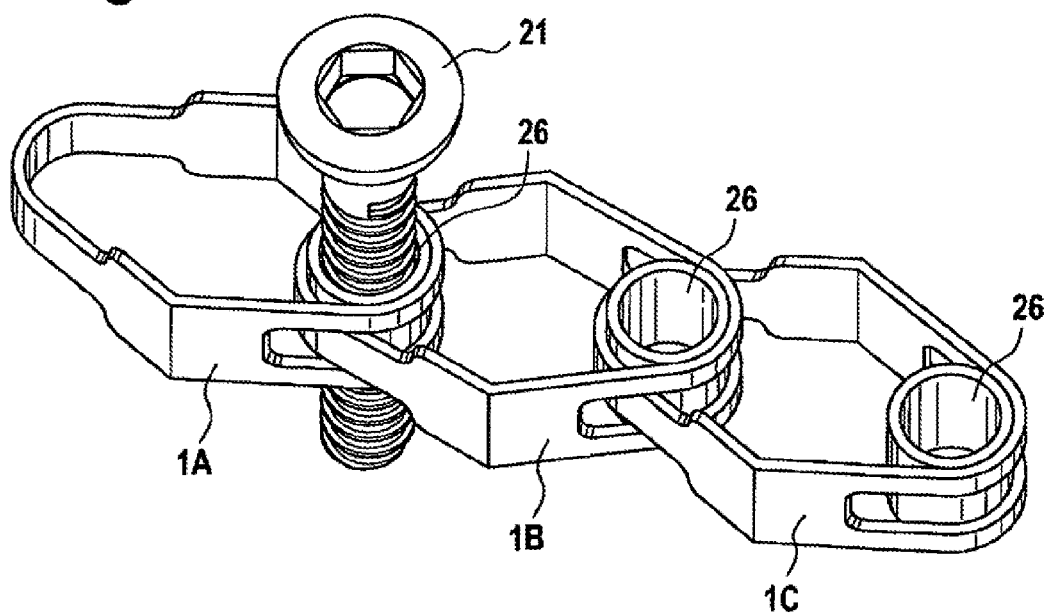
FIG. 14 is a perspective view of a setting or fixation device with absorbable sleeve elements.

FIG. 14 shows an embodiment of the setting device according to the invention, in which sleeve elements 26 made of an absorbable synthetic material are arranged between the fixing means 2 and the clamping elements 1. When the sleeve elements 26 are absorbed by the surrounding body tissue, empty spaces are produced which correspond to the sleeve elements 26. Under the tensile stress of the clamping element 1, the effective distance between the receiving portions 12 is reduced. Consequently, the pretension of the elastic clamping element 1 is cancelled so that a force decoupling between the fixing means 2 occurs. Consequently, the force transmission of the setting device vanishes with a progressing absorption of the sleeve elements 26, whereby the load onto the bones increases again.

Figure 15:
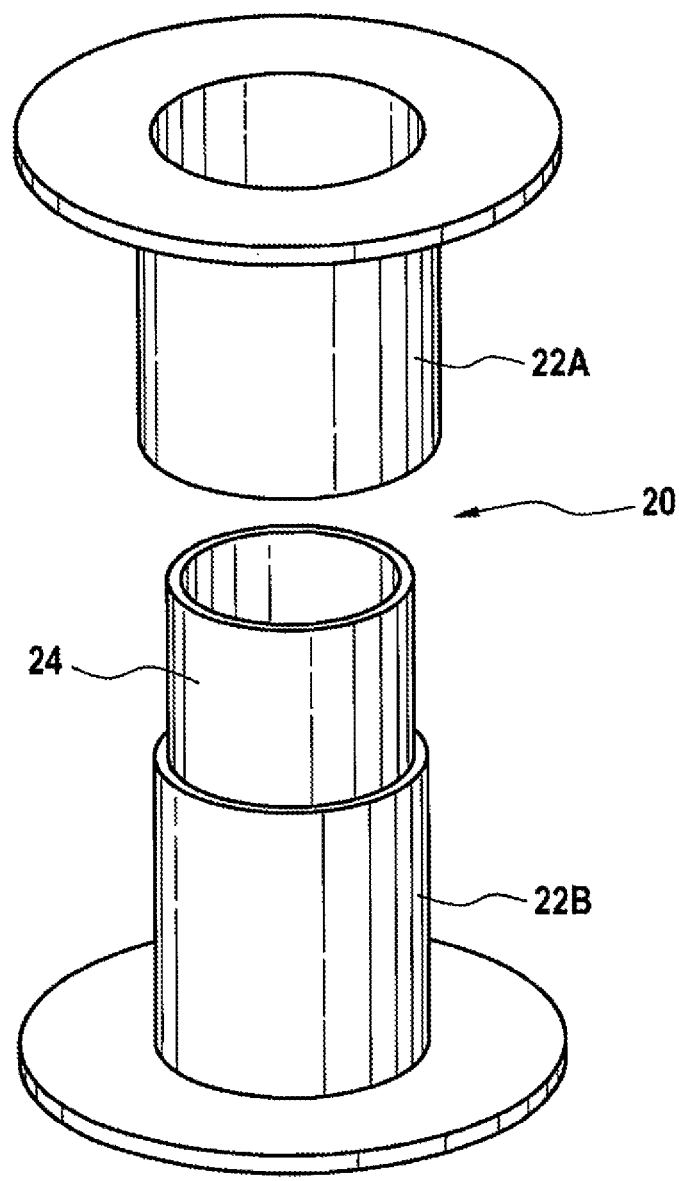
FIG. 15 is a perspective view of a radially divided clamping sleeve with an absorbable portion.

The clamping sleeve 20 in FIG. 15 comprises a radially inner section 24 in which a cortical screw 21 can be received. The radially inner section 24 is inserted into the radially outer section 22 of the clamping sleeve 20 by a fit, preferably a press fit. The radially outer section 22, in turn, can be divided into two halves 22A and 22B in the axial direction, which can be joined together by a fit. The radially inner section 24 can be made of an absorbable synthetic material and the radially outer section 22 can be made of a metal, or vice versa.

When e.g. the radially inner section 24 is absorbed, a dimensional tolerance with respect to the cortical screw 21 is created in the clamping sleeve 20. As described above, consequently the effective distance between the receiving portions 12 of the pretensioned clamping element 1 is reduced. The pretension of the clamping element 1 is cancelled, and there takes place a force decoupling of the setting device. Thus, the bone will be subjected again to an increasing strain.

The clamping sleeve 20 or one of the radially separated sections 22 and 24 thereof can be manufactured by means of a machining process, as for instance by lathe machining, from one of the above-mentioned metals. The sleeve element 26 or the other one of the two sections 22 and 24 can be cast by means of a casting process from an absorbable synthetic material. The radially divided sections 22 and 24 can be cast together with each other or can be extruded into one other. Furthermore, the clamping sleeve 20 or the radially inner section 24 also has a through-hole with an inner diameter which is determined on the basis of a diameter of a cortical screw 21.

Figure 16:
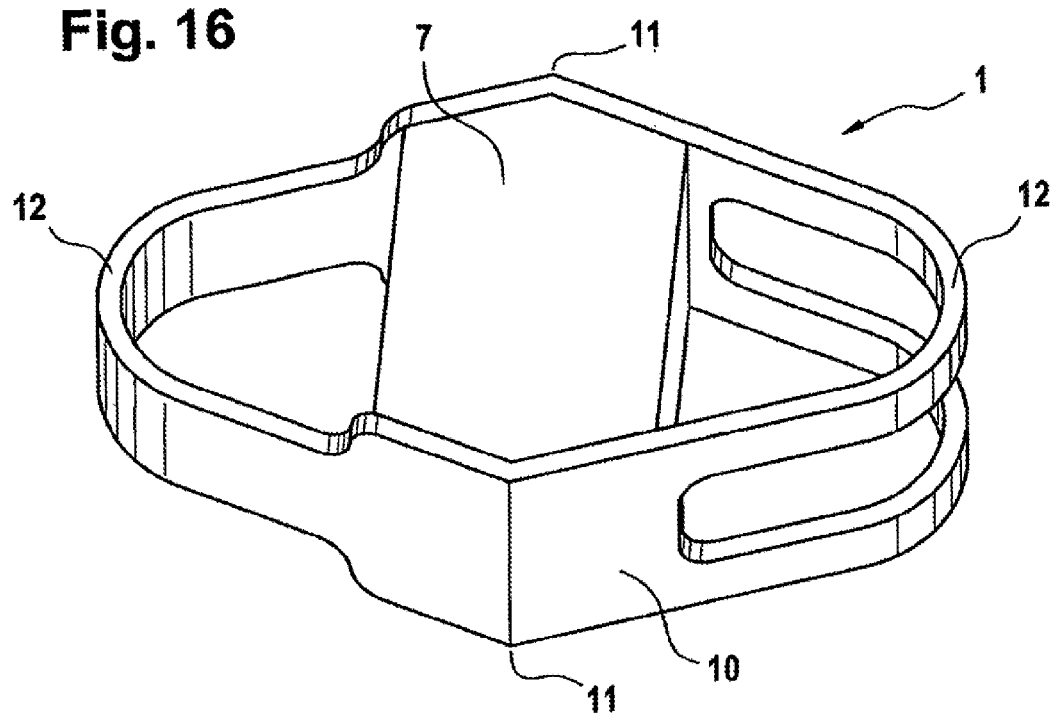
FIG. 16 is a perspective view of a clamping element with an inlay.

Furthermore, in FIG. 16 there is shown a clamping element 1 of an absorption-active setting device which loses its pretension in the course of time. To this end, an inlay 7 made of an absorbable synthetic material is provided. The inlay 7 is wedged in between the walls of the angled portions 11 when the clamping element 1 encloses the fixing means 2 (not shown). As in this variant the angled sections 11 are not pressed inwardly but outwardly in order to produce the pretension, analogously the distance between the receiving sections 12 is reduced in this case. Consequently, by the wedging of an inlay 7 with a predetermined length, a defined tractive force between the fixing means 2 can be created. When the inlay 7 is absorbed within the course of the healing process, i.e. gets shorter, etc., the angled portions 11 of the clamping element 1 return to their original released state. Consequently, the effective distance between the receiving portions 12 is increased and the tractive force between the fixing means 2 is cancelled.

Figure 17:
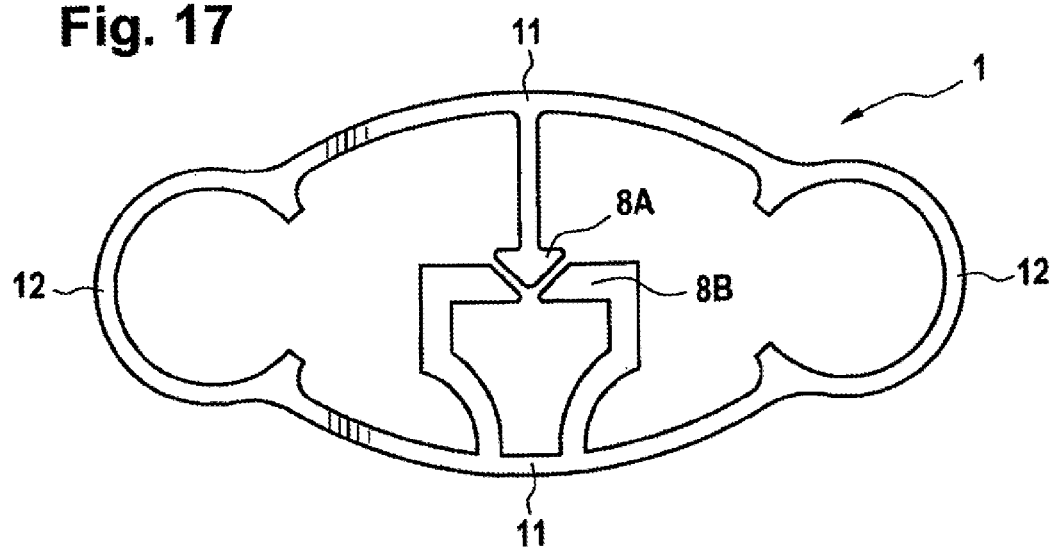
FIG. 17 is a top view of a clamping element with snap-in locking elements.

Moreover, in FIG. 17 there is shown a clamping element 1 which can be locked in a position with a predefined pretension, when the angled portions 11 are pressed towards each other. In this process, for instance an arrow-shaped element 8A snaps into a catch element 8B by means of an undercut. When a small height of the snap-in locking elements 8 is chosen, the snap-lock connection can be released or disengaged once again in a simple manner, for instance by moving the snap-in locking elements in the reverse direction in the height direction. Thereby the dimensioning of the distances of the fixing means 2 as well as the fastening of the setting device can be facilitated.

Apart from the shown embodiments, the invention also allows for further design approaches.

For instance, for the surgical operation for the fastening of the setting or fixation device a tool with several mountings can be provided into which a clamping element 1 is first of all placed. By means of a predetermined position of the lateral flanks, the clamping element 1 is held in a defined pretension. After the pushing of the fixing means 2 through the clamping element 1 and the insertion thereof in the fracture ends of the bone, the mounting of the tool can be withdrawn, whereby a predetermined tractive force acts upon the fixing means 2. Such mountings can also be provided in an individually combinable manner for an arrangement of several clamping elements 1, in order to be able to prepare a surgical operation in a time-saving manner.

Furthermore, it is also possible to constructively reinforce the clamping element 1 with a framework or bars in order to obtain a higher strength or stability of the clamping element 1 in a desired direction of strain.

Moreover, it is also possible to vary the wall cross-section of the clamping element 1 in certain sections in order to influence a local relation between elasticity and strength of the clamping element 1.

By means of the above discussed invention, a clamping element for setting or fixation of a bone fracture is provided which comprises a closed contoured body which has a substantially hollow cross-section and is enclosed by a peripheral wall which is in particular of a substantially constant thickness. The clamping element also has two opposite receiving portions at the end faces of the same, said receiving portions being intended to receive fixing means, preferably cortical screws, which can be pushed through the contoured body. Additionally, the clamping element also has two lateral flanks with angled portions, wherein the peripheral wall of the contoured body is resiliently deformable, at least in sections, in particular in the region of the receiving portions at the end faces of same and in the region of the lateral angled portions. In this connection, a defined resilient behaviour of the clamping element can be impressed via the angled portions in such a way that a predetermined tension can be generated between the receiving portions. Furthermore, according to the invention there is provided a method for producing the clamping element and a setting device for using said clamping element

What is claimed is:

1. A fixation device for bone fractures, wherein the device comprises a plurality of clamping elements and at least two fixing elements which can be inserted into a bone in a region of ends of a fracture, and wherein by a combination of several clamping elements the clamping elements can be arranged to form a chain or can be arranged in a star-shaped manner or in any combination of chain-shaped and star-shaped arrangements;

each clamping element of the plurality of clamping elements comprises a closed contoured body which has a substantially hollow cross-section and is enclosed by a peripheral wall comprising two opposite receiving portions at end faces of the contoured body, said receiving portions being intended for receiving the at least two fixing elements, and two lateral flanks having angled portions, wherein the peripheral wall of the contoured body is resiliently deformable at least in sections, a defined resilient behavior of the clamping element can be impressed via the angled portions of the lateral flanks in such a way that a predetermined tension can be generated between the receiving portions, the at least two fixing elements can be pushed through the contoured body, the receiving portions on the end faces of the contoured body are formed such that they do not enclose the at least two fixing elements, at least one of a clamping sleeve and a sleeve element is provided, in which one fixing element of the at least two fixing elements can be received, and wherein adjacent clamping elements which can be combined with each other overlap each other in such a manner that the at least two fixing elements, the at least one of the clamping sleeve and the sleeve element is enclosed by respective receiving portions on end faces of the overlapping clamping elements.

2. The fixation device of claim 1, wherein the at least two fixing elements are cortical screws.

3. The fixation device of claim 1, wherein the peripheral wall is of a substantially constant thickness.

4. The fixation device of claim 1, wherein the peripheral wall of the contoured body is resiliently deformable at least in a region of the receiving portions on end faces of the same and in a region of the angled portions of the lateral flanks.

5. The fixation device of claim 1, wherein the clamping sleeve comprises two cranks on end faces thereof, which cranks are spaced apart from each other substantially in correspondence with a wall height of a clamping element.

6. The fixation device of claim 5, wherein the clamping sleeve is formed in a two-part manner and can be joined together in an axial direction so that the peripheral wall of the clamping element can be wedged in between the cranks.

7. The fixation device of claim 5, wherein the clamping sleeve is radially divided into two sections, and a radially inner section or a radially outer section is made of an absorbable material.

8. The fixation device of claim 1, wherein the sleeve element is made of an absorbable synthetic material.

9. The fixation device of claim 1, wherein between the angled portions of at least one clamping element an inlay consisting of an absorbable material is wedged, a length of the inlay pressing apart the angled portions against a pretension of the clamping element.

10. The fixation device of claim 1, wherein an inner radius of the receiving portions at the end faces corresponds to an outer radius of a peripheral area section of the at least two fixing elements, of the sleeve element or of the clamping sleeve.

11. The fixation device of claim 1, wherein the closed contoured body of the clamping element is substantially of an oval, rhomboidal, double-rhomboidal or spectacles-shaped form.

12. The fixation device of claim 1, wherein a closed contoured body of the clamping element has a curvature with respect to a plane of extension of the contour.

13. The fixation device of claim 1, wherein in a region of the receiving portions the wall comprises at least one of openings and cutaway portions which are formed such that by at least one of a groove structure and a tongue structure of wall sections a complementary fit is provided by means of which contours of adjacent clamping elements can be caused to overlap each other.

14. The fixation device of claim 1, wherein at an outer surface of the peripheral wall coupling elements or a ball element or a spherical clamping part are provided by means of which adjacent clamping elements can be connected with each other.

15. The fixation device of claim 1, wherein at the peripheral wall there are provided fastening eyes through which the at least two fixing elements can be pushed.

16. The fixation device of claim 1, wherein at two opposing wall sections there are formed limiting bars pointing towards each other, the ends of which come into contact with each other when the clamping element is deformed.

17. The fixation device of claim 1, wherein within the contoured body of the clamping element at opposite angled portions there are arranged two snap-in locking elements which point towards each other and which can be brought into engagement with each other, by means of which the angled portions can be connected in a pretensioned position of the clamping element in a locking and again releasable or disengageable manner.

* * * * *